United States Patent [19]

Ketharanathan

[11] 4,319,363

[45] Mar. 16, 1982

[54] VASCULAR PROSTHESES

[76] Inventor: Vettivetpillai Ketharanathan, 35 Degraves St., Parkville, Victoria, Australia

[21] Appl. No.: 41,620

[22] Filed: May 23, 1979

[30] Foreign Application Priority Data

May 23, 1978 [AU] Australia ............................. PD4475

[51] Int. Cl.³ .............................................. A61F 1/00
[52] U.S. Cl. ................................... 3/1.4; 3/1; 427/2
[58] Field of Search ........................... 3/1, 1.4; 427/2

[56] References Cited

U.S. PATENT DOCUMENTS

| | | | |
|---|---|---|---|
| 3,425,418 | 2/1969 | Chvapil | 3/1.4 X |
| 3,514,791 | 6/1970 | Sparks | 3/1 |
| 3,866,247 | 2/1975 | Sparks | 3/1.4 |
| 3,866,609 | 2/1975 | Sparks | 3/1.4 |
| 3,945,052 | 3/1976 | Liebig | 3/1.4 |
| 4,098,571 | 7/1978 | Miyata | 3/1.4 |

*Primary Examiner*—Sidney Marantz
*Attorney, Agent, or Firm*—Finnegan, Henderson, Farabow, Garrett & Dunner

[57] ABSTRACT

Vascular prosthesis suitable for use as a surgical graft is produced by implanting a rod or tube in a living host animal such as a sheep and allowing collagenous tissue to grow on the implant to form a coherent tubular wall of collagenous tissue. The implant is subsequently removed and the tubular wall of collagenous tissue is stripped from the rod or tube and tanned in glutaraldehyde to serve as a vascular prosthesis.

16 Claims, 18 Drawing Figures

VASCULAR PROSTHESES

This invention relates to the field of surgery and more particularly to revascularization surgery.

The majority of deaths in the Western world are due to impaired arterial flow to distal tissues.

In the treatment of arterial disease in man, the use of a graft for myocardial revascularization and limb salvage is well accepted. Approximately 100,000 revascularization procedures for angina are being performed in the world each year. The availability of a suitable conduit is sometimes the limiting factor in the decision for coronary artery bypass surgery.

Saphenous vein bypass grafting has certain disadvantages. Death from pulmonary embolism is fortunately an infrequent consequence of vein procurement. Delayed healing of the wound, which often attends vein harvesting, is a much more frequent complication. Occasionally, haemorrhage from a branch of the venous conduit or from rupture of a defective area of vein, is an added complication. An increase in operative time associated with vein procurement is inevitable. This time loss could be critical in emergency revascularization procedures. Because of these problems, and because the saphenous vein is often unusable, unavailable or of insufficient length, a bank of vascular prostheses, available in a range of diameters, and which give results comparable to autogenous saphenous vein grafts would be highly desirable. The present invention provides this potential.

The invention broadly provides a vascular prosthesis suitable for use as a surgical graft comprising a tubular wall of Type I collagenous tissue. Preferably said wall has been subjected to glutaraldehyde tanning. The invention also extends to the use of such a vascular prosthesis as a surgical graft in a living patient.

The collagenous tissue may be ovine collagenous tissue.

The tubular wall of collagenous tissue may be reinforced with fibre mesh. Such mesh may be made of synthetic fibre such as polyester fibre. It may for example, be a tubular mesh woven from strands of multiple fine polyester fibres.

The invention also provides a method of producing a vascular prosthesis for use as a surgical graft, comprising the steps of:

implanting a rod or tube in the body of a living host animal at such a location as to cause growth of collagenous tissue thereon, allowing collagenous tissue to grow on the implanted rod or tube to form a coherent wall of said tissue, removing the rod or tube with said coherent wall of tissue from the body of the host animal, and removing the rod or tube from within the wall of collagenous tissue.

The invention further provides a method of producing a vascular prosthesis for use as a surgical graft, comprising the steps of:

positioning a tubular fibre mesh structure about a support rod or tube, implanting the mesh covered support rod or tube in the body of a living host animal at such a location as to cause growth of collagenous tissue thereon, allowing collagenous tissue to grow on the implant until there is a coherent wall of said tissue in which the mesh structure is embedded, removing the implant and said coherent wall of tissue from the body of the host animal, and removing the support rod or tube from within the tubular mesh and wall of collagenous tissue.

Preferably the host animal is a sheep and the mesh structure is a synthetic polyester fibre mesh.

Preferably too, the implant is made beneath the cutaneous muscle of the lateral thoracic wall of the host animal.

The implant may be allowed to remain in the host sheep for at least ten weeks, preferably for about twelve weeks.

The method may also include the step of tanning said wall of collagenous tissue in glutaraldehyde. This step may be carried out by immersing the implant and wall of tissue in a bath of buffered glutaraldehyde after removal from the body of the host animal and before removal of the support rod or tube.

After tanning and removal of the support rod or tube the resulting biosynthetic tube may be washed in baths of saline and hydrogen peroxide to remove all free glutaraldehyde. It may then be stored in a preservative solution, preferably a solution of alcohol or a solution comprised of propylene oxide in alcohol.

The buffered glutaraldehyde used for tanning may have a glutaraldehyde strength in the range 0.65% to 6.0% and preferably about 5%. The pH of the bath may be in the range 5.6 to 8 and is preferably about 7.4.

Buffers used to achieve the required pH may be:
1. M/15 Sodium Phosphate-Di basic $Na_2HPO_4$
2. M/15 Potassium Acid Phosphate $KH_2PO_4$ The tissue may be immersed in the buffered glutaraldehyde for between 4 hours and 72 hours, preferably for around 48 hours, and the glutaraldehyde may be washed out with a 5% Hydrogen Peroxide solution. It may be preserved in a preservative solution comprising 70% Alcohol or a solution comprising 1% Propylene Oxide and 40% Alcohol.

In order that the invention may be more fully explained the results of an experiment programme for the production and evaluation of biosynthetic grafts will be described in some detail with reference to the accompanying illustrations and Tables 1–6 of this specification. Legends for the illustrations are provided in this specification.

MATERIALS AND METHODS

The Production of Biosynthetic Grafts

Preparation of Implants

Figure 1:
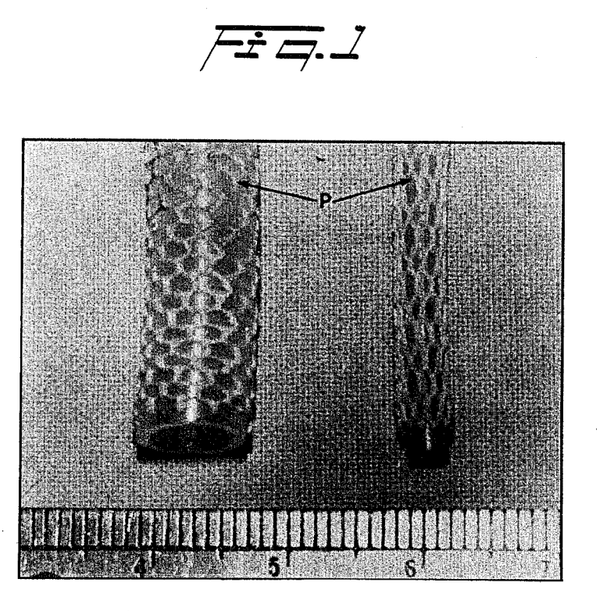
FIG. 1. Graft scaffold. Polyester mesh (P) has been stretched over a nylon cylinder (N) and silastic rod (S). The small divisions on the scale are mm.

The implants were constructed by stretching tubular polyester mesh over nylon cylinders or silastic rods of pre-determined diameter and length (FIG. 1). The composite units thus assembled were individually packaged and sterilized for implantation.

Implantation in Sheep

Figure 2:
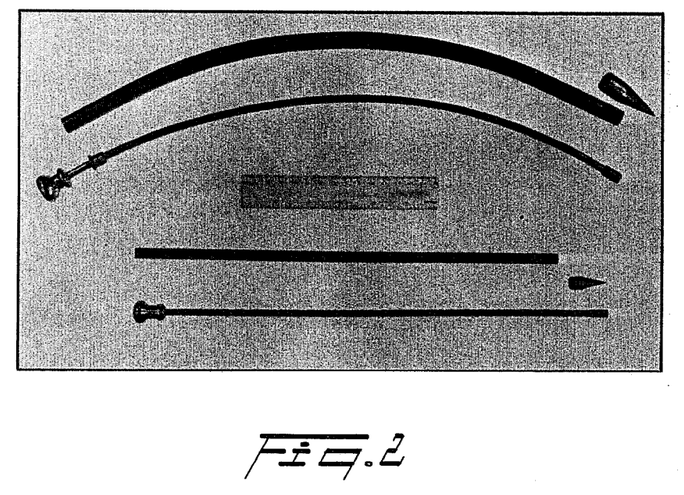
FIG. 2. Curved and straight introducers for inserting graft scaffolds.

Recently shorn crossbred male castrated sheep, in their second year, weighing between 50 and 60 kg were chosen as hosts for biosynthetic graft production. The sheep were anaesthetized and the implants were inserted aseptically, beneath the cutaneous trunci muscle of the lateral thoracic wall, with the aid of a curved introducer (FIG. 2). After three to four days of observation, the sheep were returned to the paddock where they remained for at least the next twelve weeks.

Harvesting of Biosynthetic Grafts

The sheep were sacrificed at the end of twelve weeks. The skin over the implants was prepared for surgery and draped. The implants with the adherent tissue were carefully excised and placed in physiological saline. Any excessive tissue was trimmed and then the units were placed in a bath of buffered glutaraldehyde at room temperature for 72 hours. At the end of this period the stents were removed from the units leaving behind the biosynthetic tubes. The tubes were washed in successive baths of saline and hydrogen peroxide to remove all free glutaraldehyde. A final rinse in saline completed the processing. The processed tubes (FIG. 3) were stored in one of three preservative solutions—95% alcohol, stabilized glutaraldehyde (Hancock's Solution) and 1% propylene oxide in 40% alcohol. Each solution was evaluated for its capacity to maintain the biosynthetic tubes bacteriologically sterile and free from deterioration.

THE EVALUATION OF BIOSYNTHETIC TUBES AS CANINE VASCULAR XENOGRAFTS

Healthy adult crossbred dogs weighing between 15 to 40 kg were used as recipients for biosynthetic vascular xenografts. The grafts ranged from 3 cm. to 26 cm. in length and 3 mm. to 10 mm. in diameter. They were used as segmental replacements in the external iliac artery, and as bypass grafts in two ways—abdominal aorta to external iliac artery and thoracic aorta to abdominal aorta.

A. Evaluation of Graft Lumen and Mural Integrity

1. Angiogram: A patent lumen on angiography was accepted as evidence of a functioning xenograft. This demonstrated blood flow and luminal form.
2. Preservative: For the three preservative fluids used, comparisons were made for post-operative occlusion and suture holding capacity.
3. Anastomosis Technique: In one group, at the time of graft insertion, an excised segment of iliac artery was inserted into the opposite iliac artery as an untreated autograft to control suture technique.
4. Mural Integrity of Tanned Unreinforced Collagenous Tubes:

The ability of tanned collagen tubes to withstand aortic pressure without rupturing or dilating was evaluated by inserting unsupported ovine xenografts as segmental replacements in the infrarenal abdominal aorta. The graft segments were 3 to 3.5 cm. long and anastomoses were performed with 6/0 polypropylene suture material. (Prolene, Ethicon).

B. Operative Procedures

1. Segmental Replacement of External Iliac Artery

The external iliac artery was mobilized by gentle dissection. Vascular clamps were applied and a segment of artery 1 to 2 cm. in length was excised. Elastic recoil of the cut vessel left a gap which accommodated a graft 4 to 5 cm. long. The anastomoses were performed with 7/0 polypropylene (Prolene, Ethicon) using a continuous suture technique.

2. Bypass Grafts between the Thoracic and Abdominal Aorta

Laparotomy and thoracotomy were performed simultaneously. A site for the distal anastomosis was chosen caudal to the renal arteries. The aorta was isolated by cross clamping and an end-to-side anasomosis constructed with 6/0 polypropylene using a continuous suture technique. The graft was then taken through the aortic hiatus ventral to the aorta. The appropriate anastomotic site was isolated by partial occlusion of the thoracic aorta by a tangential clamp. The proximal anastomosis was performed in the same fashion as the distal anastomosis. The aorta was ligated just cranial to the distal anastomosis.

3. Bypass Grafts between the Abdominal Aorta and External Iliac Artery

The iliac artery was mobilized by gentle dissection and isolated between vascular clamps. An end-to-side anastomosis was performed at the middle of the external iliac artery with 7/0 polypropylene using a continuous suture technique. The aortic proximal anastomosis was performed just caudal to the renal arteries.

RESULTS

A. Luminal and Mural Integrity of Tanned Unreinforced Collagenous Tubes

Figure 4A:
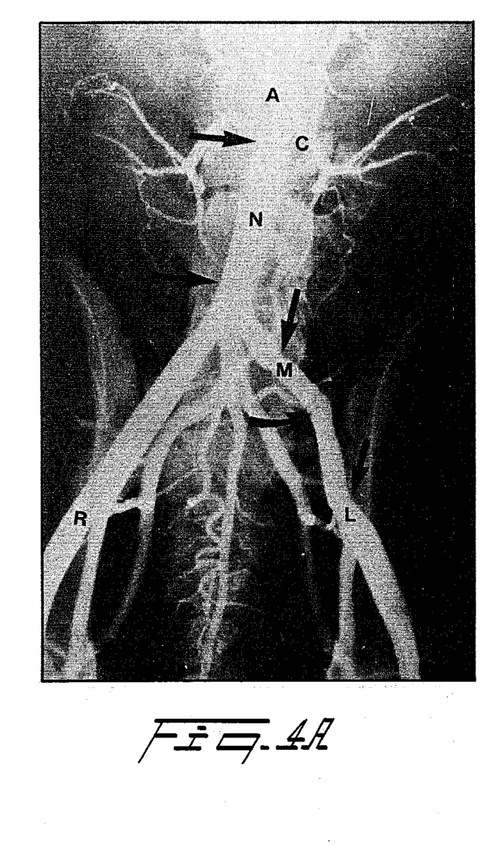
FIG. 4A. Dog 52. Angiography demonstrating two grafts, both patent 81 days after grafting. The aorta (A) and the non-mesh reinforced aortic segmental replacement graft (N) are well matched for size. There is a constriction at the proximal anastomotic site (C). The mesh reinforced iliac segmental replacement graft (M) was too long and has kinked (curved arrow), but the flow of blood to the limb through the left iliac artery (L) is comparable to the flow through the ungrafted right iliac artery (R). The limits of the grafts are marked by straight arrows.
Figure 4B:
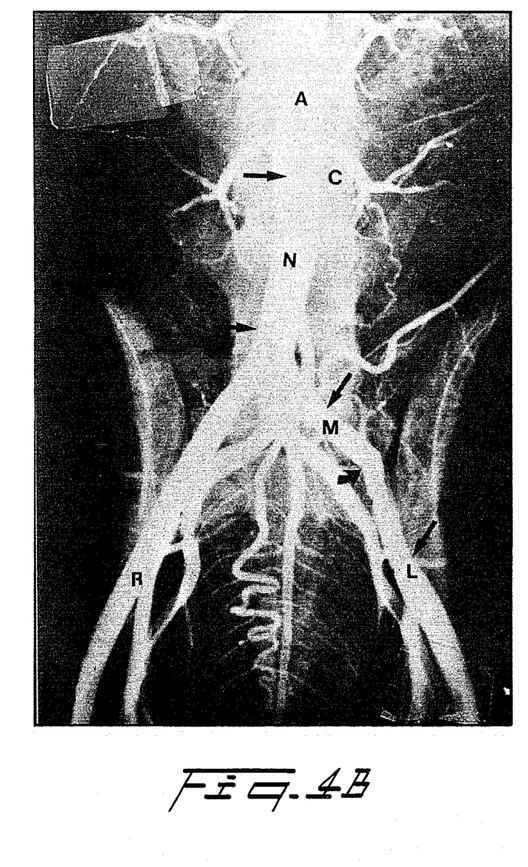
FIG. 4B. Dog 52. Angiography demonstrating two grafts, both patent 257 days after grafting. The legend is as for FIG. 4A. The flow pattern is very similar to the angiogram 81 days after grafting (FIG. 4A).
Figure 5A:
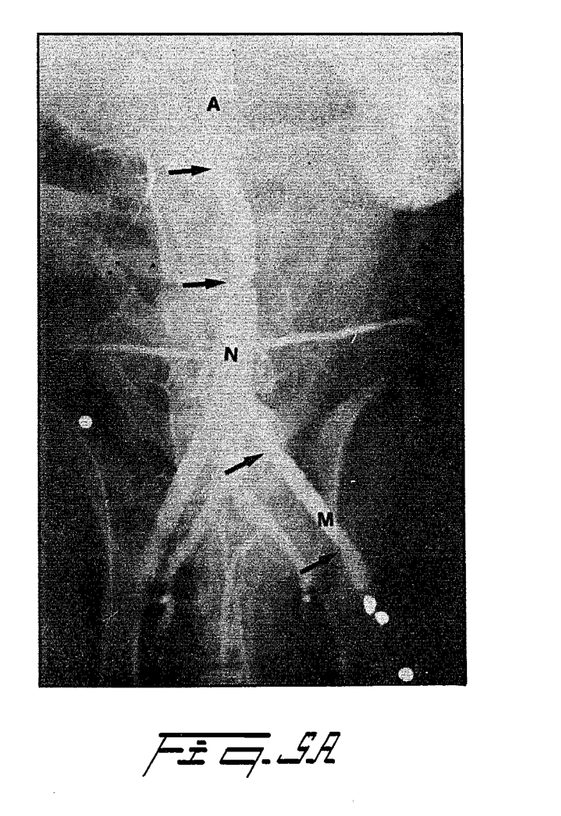
FIG. 5A. Dog 55. Angiography demonstrating two grafts both patent 70 days after grafting. The aorta (A) and non-mesh reinforced aortic segmental replacement graft (N) are mismatched. The mesh reinforced iliac graft (M) thrombosed at day 1. The thrombus was removed with an embolectomy catheter 4 days after grafting. The limits of the grafts are marked by arrows.
Figure 5B:
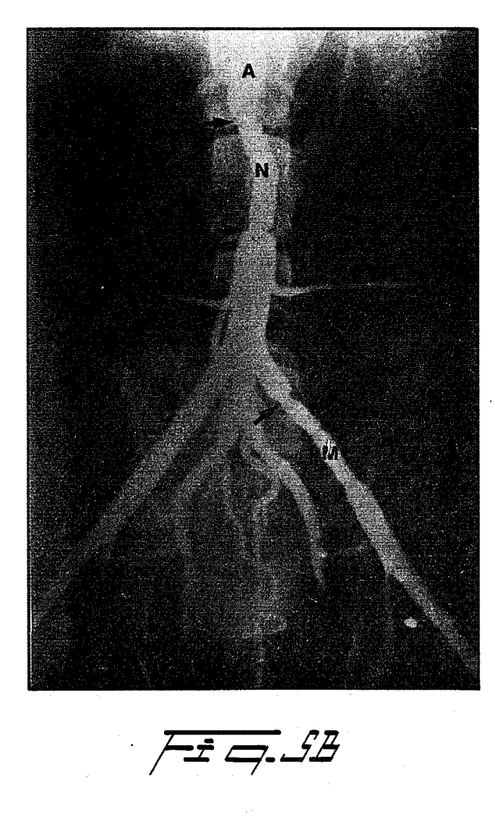
FIG. 5B. Dog 55. Angiography demonstrating two grafts both patent 300 days after grafting. The legend is as for FIG. 5A. The flow pattern has not changed since the 70 day angiogram (FIG. 5A).
Figure 6:
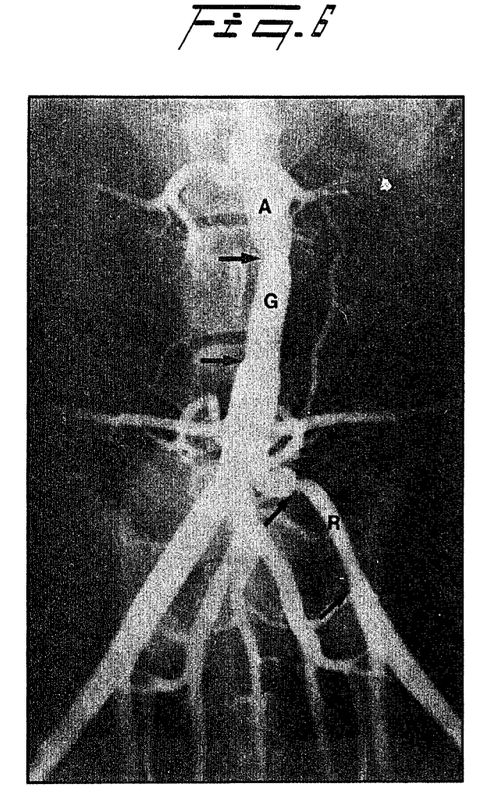
FIG. 6. Dog 70. Angiography demonstrating two grafts both patent 110 days after grafting. The aorta (A) and non-reinforced aortic graft (G) are matched. The mesh reinforced iliac graft (R) is mismatched. It thrombosed at day 1. The thrombus was removed with an embolectomy catheter 12 days after grafting. The limits of the grafts are marked by arrows.

Seven grafts were inserted as segments into the atora (Table 1). Alcohol preservation time ranged from 1 to 140 days. It was observed that sutures tended to tear the graft during anastomosis, but all grafts functioned. Over a period from 7 to 500 days the xenografts showed no narrowing or dilatation (FIGS. 4, 5, 6).

B. Alcohol Preserved Tanned Biosynthetic Xenografts

1. Iliac Segment Replacement

Figure 7:
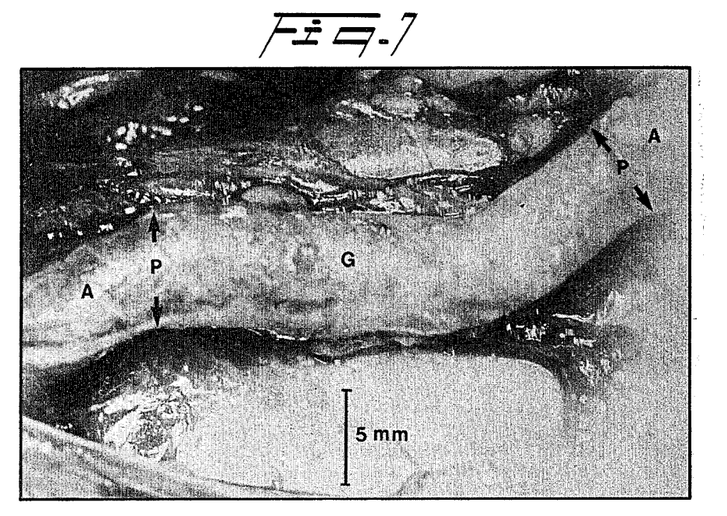
FIG. 7. Dog 52. Functioning iliac segmental replacement graft in the anaesthetized dog. The 257 days graft (G) and artery (A) appear as one unit. The reinforcing mesh which was clearly visible through the walls of the pre-implant graft (FIG. 3) is now covered by a thin layer of new fibrous tissue. The limits of the graft are marked by arrows. P is the proximal anastomosis site and D the distal anastomosis site.

Five grafts were inserted as segments into the iliac artery (Table 2). Only one of the grafts (Dog 52, FIG. 4A) had good initial function without thrombosis. The graft remained patent with pulsatile flow until the dog was sacrificed after 257 days (FIGS. 4B, 7).

Figure 8A:
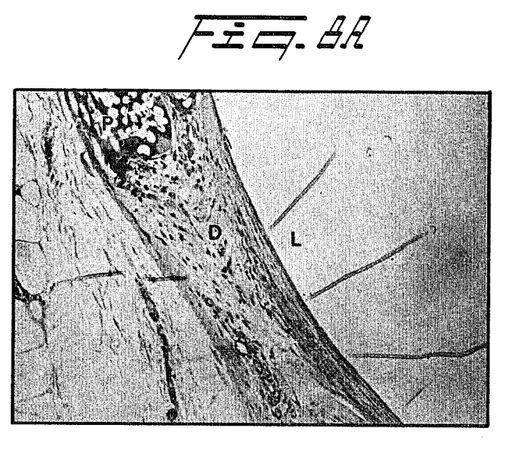
FIG. 8A. Dog 52. Pre flow graft showing polyester mesh strands (P) supporting a delicate connective tissue membrane (D). There is prominent foreign body giant cell reaction (arrow) adjacent to the mesh and there is a smooth lining to the lumen (L). Magn. ×400.
Figure 8B:
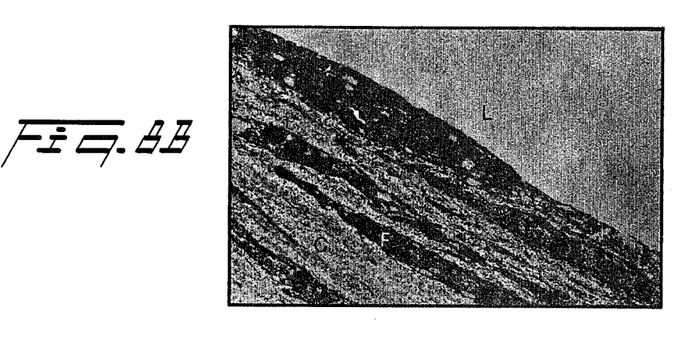
FIG. 8B. Dog 52. Ultrastructural detail of pre flow graft showing closely packed laminated layers of collagen bundles (C) with numerous fibroblasts (F), some of which line the lumen (L). Magn. ×5000.
Figure 9:
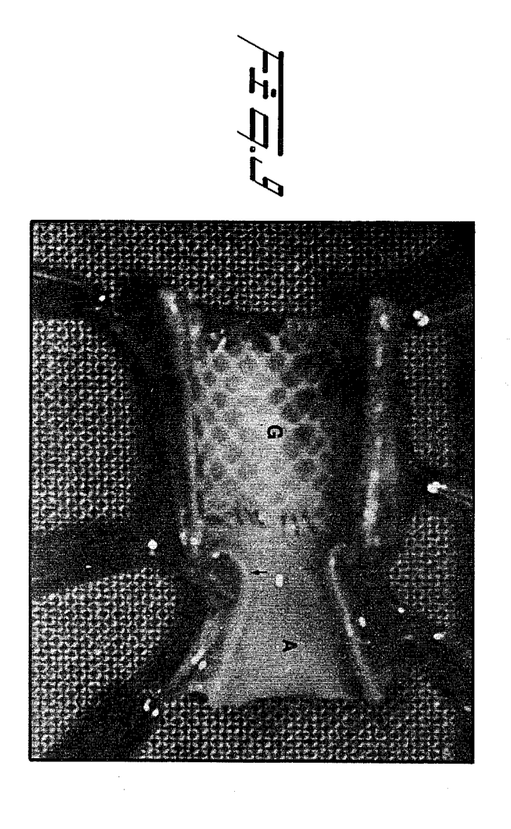
FIG. 9. Dog 52. Showing the luminal surface of a biosynthetic craft which functioned as a vascular conduit for 257 days. The lining of both artery (A) and graft (G) is smooth. The artery has a post mortem constriction (arrows). The arterial wall and graft wall are of comparable thickness and the reinforcing mesh is still clearly visible.
Figure 10A:
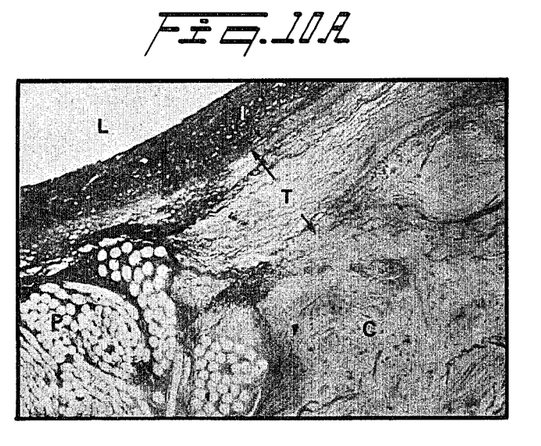
FIG. 10A. Dog 52. Section through a tanned graft after 257 days flow. L indicates the lumen. A broad area of visible tissue forms the new intima (I). External to this, there is loose myxoid filbrillar material which is the former tanned collagenous tube (T), lying adjacent to the polyester strand of the mesh (P). Outside this region there is new viable collagenous tissue (C). Broad bundles of fresh collagen fibres are associated with numerous fibroblasts. Magn. ×400.
Figure 10B:
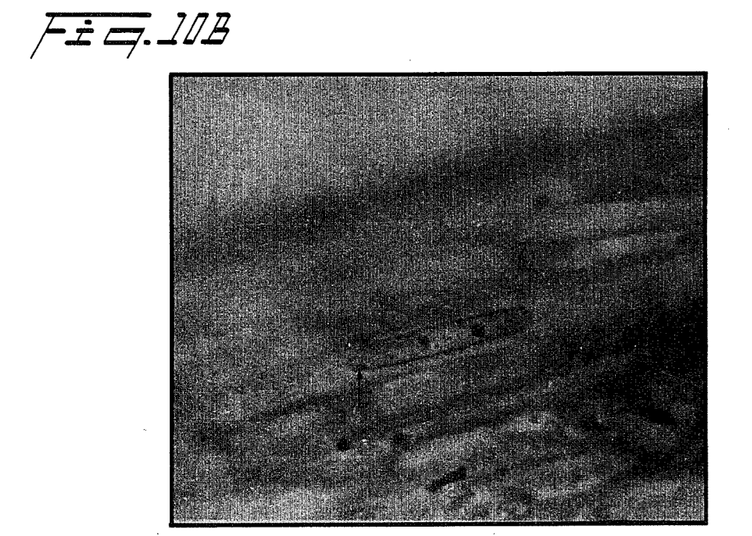
FIG. 10B. Detail of cells in the new intima zone (I in FIG. 10A) of host origin showing well preserved nucleus, prominent nucleolus and Barr body (arrow). Magn. ×3,600.
Figure 10C:
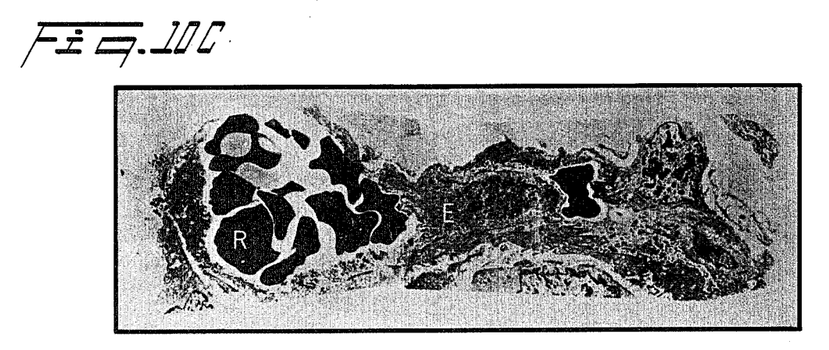
FIG. 10C. Shows detail of the post-flow graft endothelial lining. An ultrastructural montage of a tangential cut shows the lumen indicated by the presence of red cells (r), lined by cells with typical endothelial characteristics (E). (magn. ×12,500 reduced to 2,500).

The wall of the pre-flow graft is composed of mature collagen with a smooth inner surface (FIG. 8). After functioning as a vascular conduit for 257 days, the graft has become lined with multiple layers of endothelium and the wall has been reinforced by new collagen (FIGS. 9, 10).

The other four grafts occluded within 24 hours. Dog 55 had a thrombectomy four days after grafting and the graft has now remained patent in excess of 500 days (FIG. 5B). Dog 70 had a thrombectomy on day 12 and that graft has also remained patent in excess of 500 days (FIG. 6).

2. Aorto-Iliac Bypass Grafts

Figure 11A:
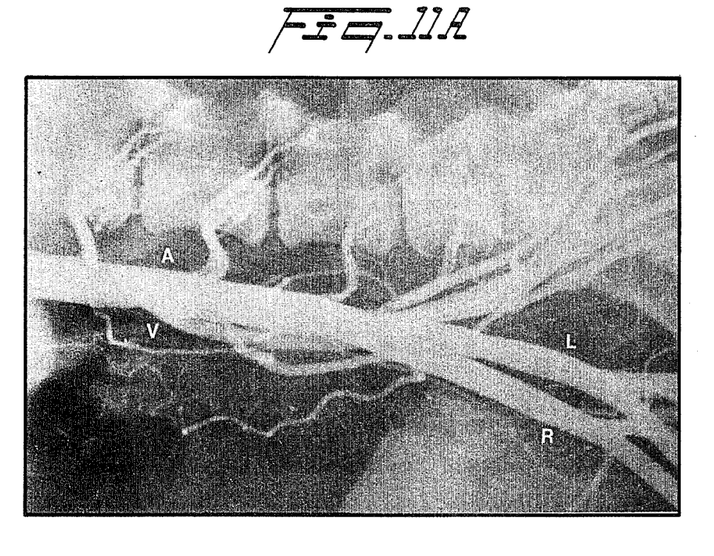
FIG. 11A. Dog 93. Aorto-iliac bypass graft. Lateral angiogram demonstrating patency 20 days after grafting. The graft (V) is seen coming off the ventral surface of the aorta (A) to provide full flow to the left iliac artery (L), comparable to the flow through the ungrafted right iliac artery (R).
Figure 11B:
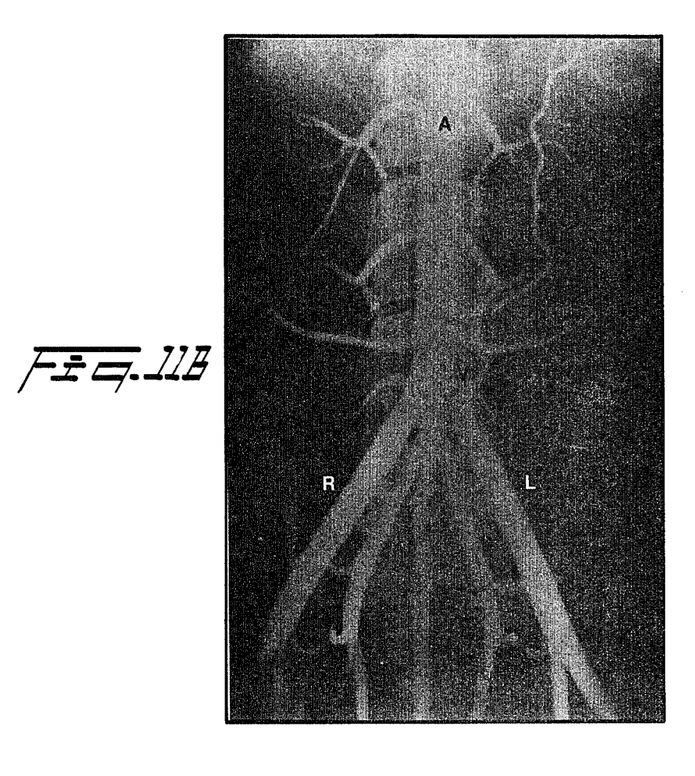
FIG. 11B. Dog 93. Aorto-iliac bypass graft. Ventrodorsal angiogram demonstrating patency 179 days after grafting. The graft (V) is concealed at its proximal anastomosis by the aorta (A) but can be seen anastomosing with the left iliac artery (L) to provide full flow, comparable to that through the ungrafted right iliac artery (R).

Five grafts were inserted (Table 3). Only one of the grafts (Dog 93) had good initial function without thrombosis. It has remained patent in excess of 400 days (FIG. 11).

C. Glutaraldehyde Preserved Tanned Biosynthetic Xenografts with Unmodified Iliac Autografts as Controls Five dogs had glutaraldehyde preserved biosynthetic graft segments inserted in the left external iliac artery (Table 4). At the same operation unmodified iliac artery segments were inserted as replacement autografts in the right external iliac artery as controls on technique. The initial patency rate for the iliac autograft controls was 4 in 5 or 80%. The glutaraldehyde preserved biosynthetic xenografts all thrombosed.

D. Comparison of Glutaraldehyde and Propylene Oxide/Alcohol as Preservatives for Biosynthetic Iliac Xenografts Five dogs had paired grafts inserted (Table 5). Immediate graft function was good in all dogs but 4 of the glutaraldehyde preserved grafts thrombosed between one hour and three days after grafting—a patency rate of 20%. In contrast, 4 of the 5 propylene oxide/alcohol preserved grafts have functioned in excess of 280 days-a patency rate of 80%.

E. Propylene Oxide/Alcohol Preservation of Biosynthetic Xenografts as Bypass Grafts

1. Aorto Iliac Bypass

This procedure was attempted on four dogs (Table 6). One graft failed within one hour due to faulty technique. The other three grafts had good initial function with strong femoral pulses. However, pulsations stopped suddenly and unexpectedly on day four in two dogs and day six in one dog. Autopsies showed that in each case, fat which had been traumatized during the grafting procedure had, during the healing process, surrounded the graft and constricted it.

2. Thoracic Aorta to Abdominal Aorta Bypass

Figure 12:
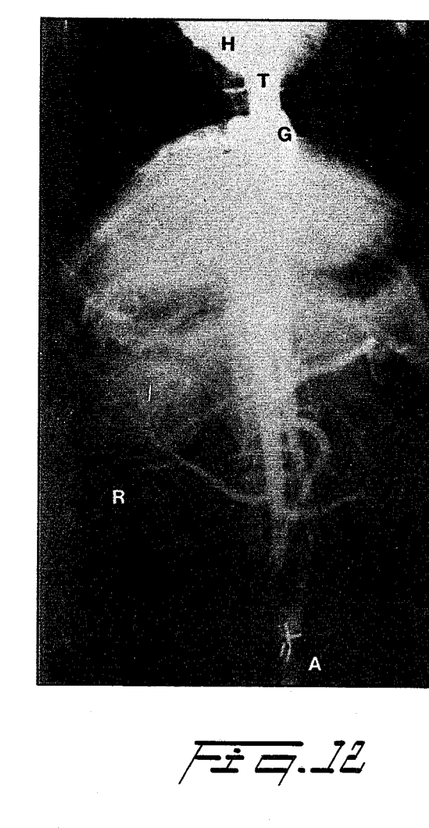
FIG. 12. Dog 95. Thoracic aorta to abdominal aorta by-pass. Angiogram demonstrating patency 13 days after grafting a 25 cm. long conduit. The graft (G) arises from the thoracic aorta (T) to supply the infrarenal abdominal aorta (A), which had been occluded with haemoclips. Other structures labelled are the right kidney (R) and heart (H).

This procedure was attempted on three dogs. One dog died on the table as a result of faulty technique. A graft 25 cm. long and 8 mm. in diameter inserted into dog number 95/77 had good initial function and has remained patent in excess of 90 days (FIG. 12). A 22 cm. long, 6 mm. diameter graft inserted into dog 108/77 had good initial function but pulsations suddenly ceased on day 4 and the dog was acutely lame. Abdominal exploration showed that the distal anastomosis was occluded by constricting fatty adhesion.

The results of the test programme indicate that polyester mesh reinforced collagen tubes can successfully replace arteries 3 to 8 mm. in diameter as xenografts in dogs. These tubes are economic to produce in sheep and have uniform thickness and calibre. After glutaraldehyde tanning and propylene oxide alcohol preservation, they may be stored for extended periods at room temperature to provide readily available pretested conduits of varying diameters and lengths. Each sheep can grow up to 4.5 meters of reinforced collagen tubing in 30 cm. lengths or 3.6 meters in 60 cm. lengths.

In this study three preserving solutions were evaluated; 95% alcohol, stabilized glutaraldehyde, and 1% propylene oxide in 40% alcohol. Grafts stored in absolute alcohol for over 100 days functioned satisfactorily as aortic interposition and aorto-iliac bypass grafts. However, such grafts tended to tear during anastomosis. Also, with increased storage time, there was a fatty sedimentation in the preserving fluid and patchy deposition of an amorphous substance on the lining of the grafts. Grafts stored in stabilized glutaraldehyde retained good suture holding capacity but they showed a high incidence of early thrombosis when used as small calibre (3–5 mm.) artery replacements. When storage solution was changed to 1% propylene oxide in 40% alcohol, the grafts handled well at operations and there was a dramatic reduction in early thrombosis from 100% to 20%.

The desirable features of the ovine reinforced collagen conduit revolve around glutaraldehyde tanning. Tanning modifies the raw collagen and greatly improves its handling characteristics. It also imparts strength, immunological inertness and sterility to the graft.

The increased strength is due to cross linking of the collagen fibrils. The inherent strength of the processed grafts was investigated by inserting unreinforced tubes as aortic segmental replacements in dogs. All grafts remained patent for the duration of the observation (Table 1) and especially significant was the observation that there were no signs of graft disintegration, dilatation or rupture for period in excess of 500 days. The fine polyester mesh was incorporated into the graft to ensure uniform and even growth of the collagen and to enhance structural integrity. There was no angiographic evidence of dilatation in the long term functioning grafts—including those which were subjected to thrombectomy because of early thrombosis. The xenografts which had functioned as iliac and aortic conduits for 257 days (Dog 52) showed no gross or microscopic evidence of degeneration. The graft wall had increased in thickness due to collagen deposition on the outside (FIGS. 7, 9, 10). This did not alter the lumen (FIGS. 4, 9).

Previous research work suggests that glutaraldehyde tanning alters the antigen combining sites thereby shielding the xenograft from immune reaction. No mononuclear cellular infiltrates have been identified in the ovine graft tissues harvested so far. This suggests that the immunogenicity of this material is very low.

In addition to tanning, glutaraldehyde is a most efficient sterilizing agent. However propylene oxide was added to the alcohol preserving solution to ensure that sterility was maintained. This was confirmed by subjecting grafts which had been in preserving solution for 1 year to aerobic and anaerobic bacterial culture. No organisms grew.

All graft failures from all causes occurred within one week. If the grafts were patent at the end of one week they continued to remain patent. Three causes of graft failure become apparent—poor technique, glutaraldehyde residues and omental strangling. The graft and recipient vessel need to be handled gently and the graft kept moist, otherwise it becomes brittle and could tear. For vessels less than 5 mm. diameter, a $\times 2$ magnifying loop was an aid to accurate anastomosis. Glutaraldehyde residues remaining on the graft were strongly thrombogenic. Patency rates improved from 20% to 80% when the storage solution was changed from stabilized glutaraldehyde to propylene oxide and alcohol. Grafts passing through the chest and abdominal cavities can be constricted by adhesions. To minimize this possibility, careful siting of the graft and minimal surgical trauma are required.

In its present form, tanned and preserved ovine collagen tubes could be used as vascular xenografts in man for limb salvage, myocardial revascularization, venous replacement and therapeutic arteriovenous fistulae. Two grafts have in fact functioned for more than 6 months in two sites in a human patient with superior vena caval obstruction. In another human patient, a 50 cm. arterial graft has functioned satisfactorily, saving a leg which would otherwise have required amputation.

TABLE 1

AORTIC SEGMENTAL REPLACEMANT GRAFTS USING TANNED ALCOHOL PRESERVED OVINE COLLAGEN XENOGRAFTS WITHOUT MESH SUPPORT

| DOG NUMBER | GRAFT INTERNAL DIAMETER (mm.) | GRAFT LENGTH (cm.) | PRESERVATIVE | PRESERVATION TIME | RESULT |
|---|---|---|---|---|---|
| 37/76 | 6.3 | 3.5 | 95% alcohol | 14 days | Patent 56 days - sacrificed |
| 44/76 | 6.3 | 3.5 | 95% alcohol | 42 days | Patent 6 days - sacrificed |
| 52/76 | 8.6 | 3.5 | 95% alcohol | 56 days | Patent 257 days - sacrificed |
| 55/76 | 8.6 | 3.1 | 95% alcohol | 14 days | Patent 554 days - continuing |
| 54/76 | 8.6 | 3.5 | 95% alcohol | 1 day | Patent 14 days - sacrificed |
| 70/76 | 10.2 | 3.0 | 95% alcohol | 50 days | Patent 500 days - continuing |
| 78/76 | 8.6 | 3.5 | 95% alcohol | 140 days | Patent 35 days - sacrificed |

TABLE 2

ALCOHOL PRESERVED BIOSYNTHETIC XENOGRAFTS - ILIAC SEGMENTAL REPLACEMENT

| DOG NUMBER | GRAFT INTERNAL DIAMETER (mm.) | ALCOHOL PRESERVATION TIME (DAYS) | RESULT |
|---|---|---|---|
| 52/76 | 4.3 | 56 | Patent 257 days - sacrificed. |
| 55/76 | 4.3 | 14 | Thrombosed day 1. thrombectomy day 4. Continued patency in excess of 500 days. |
| 54/76 | 4.3 | 1 | Thrombosed day 1. Sacrificed on 15th day. |
| 70/76 | 4.3 | 50 | Thrombosed day 1. Thrombectomy day 12. Continued patency in excess of 500 days. |
| 78/76 | 3.2 | 140 | Thrombosed day 1. Sacrificed on 35th day. |

Initial patency rate 1 in 5 or 20%

TABLE 3

ALCOHOL PRESERVED TANNED BIOSYNTHETIC XENOGRAFTS - AORTO-ILIAC BYPASS

| DOG NUMBER | GRAFT INTERNAL DIAMETER (mm.) | GRAFT LENGTH (cm.) | ALCOHOL PRESERVATION TIME (DAYS) | RESULT |
|---|---|---|---|---|
| 86/76 | 3.5 | 10.0 | 161 | Thrombosed day 1 - sacrificed |
| 88/76 | 3.5 | 10.0 | 99 | Thrombosed day 1 - sacrificed |
| 93/76 | 4.0 | 8.0 | 113 | Patent in excess of 400 days. |
| 95/76 | 4.0 | 9.0 | 190 | Thrombosed day 1. |
| 97/76 | 3.5 | 10.0 | 147 | Thrombosed day 1. |

Patency rate 1 in 5 or 20%

TABLE 4

GLUTARALDEHYDE PRESERVED TANNED BIOSYNTHETIC XENOGRAFTS WITH UNMODIFIED ILIAC AUTOGRAFTS AS CONTROLS

| DOG NUMBER | GRAFT INTERNAL DIAMETER (mm.) | PATENCY Iliac autograft | Iliac xenograft |
|---|---|---|---|
| 15/77 | 4.0 | In excess of 21 days - sacrificed | Less than 3 days. |
| 17/77 | 4.0 | In excess of 14 days - sacrificed | 1 day. |
| 20/77 | 3.5 | In excess of 7 days - sacrificed | Clotted day 1. Embolectomy day 3. Patent in excess of 7 days. |
| 27/77 | 4.0 | 1 day - sacrificed | 1 hour. |
| 31/77 | 3.5 | In excess of 1 day - sacrificed | 1 hour |
| | Initial patency rate | 4 in 5 or 80% | 0-5 or 0% |

TABLE 5
COMPARISON OF GLUTARALDEHYDE AND PROPYLENE OXIDE/ALCOHOL AS PRESERVATIVES FOR TANNED BIOSYNTHETIC ILIAC XENOGRAFTS.

| DOG NUMBER | GRAFT INTERNAL DIAMETER (mm.) | GRAFT PRESERVATION TIME (DAYS) | PATENCY Left external iliac segment (Glutaraldehyde preserved) | PATENCY Right external iliac segment (Propylene oxide alcohol preserved) |
|---|---|---|---|---|
| 40/77 | 3.5 | 14 | 1 hour | In excess of 280 days. |
| 43/77 | 3.5 | 21 | Less than 3 days | In excess of 270 days. |
| 46/77 | 4.5 | 28 | 1 day | In excess of 260 days. |
| 49/77 | 4.5 | 35 | Less than 3 days | Less than 3 days. |
| 54/77 | 3.5 | 42 | In excess of 240 days | In excess of 240 days. |
| | | Patency rate | 1 in 5 or 20% | 4 in 5 or 80% |

TABLE 6
PROPYLENE OXIDE/ALCOHOL PRESERVATION OF TANNED BIOSYNTHETIC XENOGRAFTS AS AORTO-ILIAC BYPASS GRAFTS.

| DOG NUMBER | GRAFT DIAMETER (mm.) | GRAFT LENGTH (cm.) | PROPYLENE OXIDE ALCOHOL PRESERVATION TIME (DAYS) | RESULTS |
|---|---|---|---|---|
| 64/77 | 4.3 | 10 | 30 | Clotted 1 hour. Technical failure. |
| 69/77 | 4.3 | 13.5 | 44 | Strong pulse day 3, occluded day 4 due to external compression. |
| 76/77 | 4.3 | 11.5 | 126 | Strong pulse day 3, occluded day 4 due to external compression. |
| 80/77 | 4.3 | 10 | 70 | Strong pulse day 5, occluded day 6 due to external compression. |

BRIEF DESCRIPTION OF THE FIGURES

FIG. 3. Processed preserved biosynthetic tube ready for use as a vascular graft. The ovine collagen (C) has formed a tube whose walls are of uniform thickness. The polyester mesh is incorporated within the collagen wall but can still be clearly seen through both the luminal surface (L) and the outer surface (O). The small divisions on the scale are mm.

I claim:

1. A vascular prosthesis suitable for use as a surgical graft in a human patient, comprising:
   a coherent tubular wall of non-human Type I collagenous tissue which has been subjected to glutaraldehyde tanning so as to comprise cross-linked collagen fibrils, and
   a tubular reinforcement of fibre mesh embedded within the coherent wall of tanned collagenous tissue.

2. A vascular prosthesis as claimed in claim 1, wherein the collagenous tissue is ovine collagenous tissue.

3. A vascular prosthesis as claimed in claim 1, wherein said mesh is a tubular mesh woven from strands of multiple fine polyester fibres.

4. A method of revascularization surgery wherein a vascular prosthesis as defined in claim 1 is used as a surgical graft in a living patient.

5. A method of producing a vascular prosthesis suitable for use as a surgical graft in a human patient, comprising the steps of:
   implanting a rod or tube in the body of a living non-human, host animal at such a location as to cause growth of Type I collagenous tissue thereon;
   allowing said collagenous tissue to grow on the implanted rod or tube to form a coherent wall of said tissue;
   removing the rod or tube with said coherent wall of tissue from the body of the host animal;
   subjecting said coherent wall of collagenous tissue to glutaraldehyde tanning in order to produce cross-linking of collagen fibrils therein so as to increase the strength of the wall and also to impart immunological inertness and sterility thereto; and
   removing the rod or tube from within the coherent wall of collagenous tissue at any time subsequent to the removal of the rod or tube and coherent wall of collagenous tissue from the body of the host animal.

6. A method as claimed in claim 5, wherein a wall reinforcing structure is positioned on the rod or tube before it is implanted in the body of the host animal such that the wall reinforcing structure becomes embedded in said coherent wall of collagenous tissue.

7. A method of revascularization surgery wherein a vascular prosthesis produced by the method of claim 5 is used as a surgical graft in a living patient.

8. A method of producing a vascular prosthesis suitable for use as a surgical graft in a human patient, comprising the steps of:
   positioning a tubular synthetic fibre mesh structure about a support rod or tube;
   implanting the mesh covered support rod or tube in the body of a living, non-human, host animal at such a location as to cause growth of Type I collagenous tissue thereon;
   allowing said collagenous tissue to grow on the implant until there is formed a coherent wall of said tissue encompassing the rod or tube and having the mesh structure embedded therein;
   removing the implant and said coherent wall of collagenous tissue from the body of the host animal;
   subjecting said coherent wall of collagenous tissue to glutaraldehyde tanning in order to produce cross-linking of collagen fibrils therein so as to increase the strength of the wall and also to impart immunological inertness and sterility thereto; and
   removing the rod or tube from within the coherent wall of collagenous tissue at any time subsequent to removal of the rod or tube and coherent wall of collagenous tissue from the body of the host animal.

9. A method as claimed in claim 8, wherein the host animal is a sheep.

10. A method as claimed in claim 9, wherein the implant is made beneath the cutaneous muscle of the lateral thoracic wall of the host animal.

11. A method as claimed in claim 9, wherein the implant is allowed to remain in the host animal for at least ten weeks.

12. A method as claimed in claim 8, wherein the tanning step is carried out by immersing the implant and wall of tissue in a bath of buffered glutaraldehyde after removal from the body of the host animal and before removal of the support rod or tube.

13. A method as claimed in claim 12, wherein the buffered glutaraldehyde used for tanning has a glutaraldehyde strength in the range 0.65% to 6.0%.

14. A method as claimed in claim 12, wherein the pH of said bath is in the range 5.6 to 8.

15. A method as claimed in claim 12, wherein the implant and wall of tissue are immersed in said bath for between 4 hours and 72 hours and residual glutaraldehyde is washed out of the tissue with a hydrogen peroxide solution.

16. A vascular prosthesis suitable for use as a surgical graft in a human patient, comprising:

a coherent tubular wall of non-human Type I collageous tissue which has been subjected to glutaraldehyde tanning so as to comprise cross-linked collagen fibrils.

* * * * *